United States Patent [19]
Berger et al.

[11] Patent Number: 5,736,583
[45] Date of Patent: Apr. 7, 1998

[54] FUNCTIONAL SILICONE FLUIDS CONTAINING A CARBOXYL FUNCTIONAL GROUP THEREON

[75] Inventors: Abe Berger, Summit; Dennis L. Fost, Ridgewood, both of N.J.

[73] Assignee: Mona Industries, Inc., Paterson, N.J.

[21] Appl. No.: 784,308

[22] Filed: Jan. 16, 1997

Related U.S. Application Data

[63] Continuation-in-part of Ser. No. 420,746, Apr. 12, 1995, Pat. No. 5,596,061.
[51] Int. Cl.⁶ .................................................. C08G 77/04
[52] U.S. Cl. .......................... 528/26; 528/25; 528/38; 548/406; 514/772
[58] Field of Search ............................ 528/26, 25, 38; 548/406; 514/772

[56] References Cited

U.S. PATENT DOCUMENTS 5,596,061  1/1997  Berger et al. ............................ 528/26

*Primary Examiner*—Melvyn I. Marquis
*Attorney, Agent, or Firm*—Franklyn Schoenberg; Norman E. Lehrer

[57] ABSTRACT

An uncapped polysiloxane composition is provided having the formula:

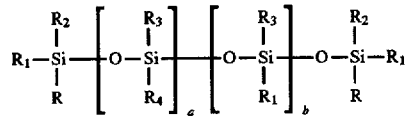

wherein:

R is selected from $R_2$ or $-OR_9$ wherein $R_9$ is hydrogen or alkyl;

$R_1$ is selected from $R_2$, an amine containing group of the formula $-(CH_2)_n-F_{n1}-B_{n2}-F-NH_2$ functional carboxyl group of the general formula:

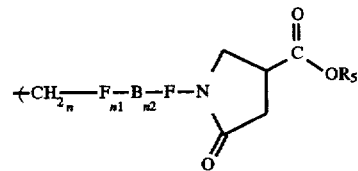

wherein at least one $R_1$ is a pyrrolidone-containing functional carboxyl group as shown; $R_2$ is as defined below; $R_5$ is hydrogen, alkyl or alkali metal; F is linear or branched alkylene; B is $-NR_9$, oxygen or sulfur, wherein $R_9$ is hydrogen or lower alkyl ($C_{1-6}$);

$R_2$ can be the same or different and is selected from alkyl, aryl, alkenyl or alkeynyl;

$R_3$ and $R_4$, are selected from alkyl, aryl, capped or uncapped polyoxyalkylene, alkaryl, aralkylene or alkenyl;

a is an integer from 0 to 50,000; and b is an integer from 0 to 100.

19 Claims, No Drawings

FUNCTIONAL SILICONE FLUIDS CONTAINING A CARBOXYL FUNCTIONAL GROUP THEREON

RELATED APPLICATION

This application is a continuation in part of application Ser. No. 420,746, filed Apr. 12, 1995, U.S. Pat. No. 5,596,061.

FIELD OF THE INVENTION

The present invention relates to novel organosilicone compositions and, more particularly, to silicone compositions having a carboxyl functional group thereon.

BACKGROUND OF THE INVENTION

Carboxyl functional organosilicones are known, but they are generally difficult and expensive to prepare and the commercial use thereof has therefore been limited. Heretofore, no convenient method for preparing polysiloxanes containing functional carboxylic acid groups has been known and indirect routes for their preparation have generally been used, such as hydrosilylation of an unsaturated ester followed by hydrolysis, or alternatively, by hydrolysis of nitrile-containing silicone fluids. However, polysiloxanes, both capped and uncapped, containing one or more carbofunctional groups such as amino and diamino groups are well known and have been used in a variety of commercial applications, but few of such polysiloxanes also contain carbofunctional carboxyl groups or provide an amphoteric class of said organosilicones. Accordingly, the development of a method for readily preparing both capped and uncapped, polysiloxane fluids containing one or more carbofunctional carboxyl groups would be desirable and it would be particularly advantageous if such method employed readily available silicone materials such as amino and diamino functional polysiloxanes for preparing not only a variety of capped polysiloxanes containing carbofunctional carboxyl groups including an amphoteric class of such organosiloxanes but uncapped siloxanes containing carbofunctional carboxyl groups as well including a variety of derviatives thereof.

While, as indicated, certain capped and uncapped polysiloxanes containing carbofunctional carboxylic acid groups and methods for preparing the same have heretofore been suggested, there is no disclosure or suggestion of the novel capped silicone compositions containing carbofunctional carboxyl groups or the method of preparing the same described in copending application Ser. No. 420,746 of which the present application is a continuation in part, or of the novel uncapped polysiloxanes containing carbofunctional carboxyl groups of the present invention including an amphoteric class of such silicone compositions.

SUMMARY OF THE INVENTION

It is accordingly an object of the present invention to provide novel uncapped organosilicone compositions having at least one carbofunctional carboxyl group thereon.

It is another object of the present invention to provide novel uncapped polysiloxane compositions having at least one novel carbofunctional pyrrolidone-containing carboxyl group or the ester thereof.

It is a further object of the present invention to provide a novel amphoteric class of uncapped organosilicone compositions.

It is a further object of the present invention to provide a method for readily preparing uncapped organosilicone compositions having at least one carbofunctional pyrrolidone-containing carboxyl group thereon including an amphoteric class of uncapped organosilicone compositions.

In accordance with the present invention, there has now been discovered novel uncapped polysiloxanes containing one or more carboxylic acid groups and/or the ester derivatives thereof that may be represented by the following general formula:

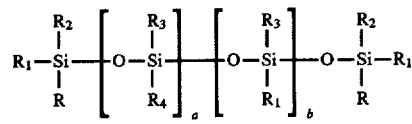

wherein:

R is selected from $R_2$ or $—OR_9$ wherein $R_9$ is hydrogen or alkyl, with the proviso that at least one of the R groups must be $—OR_9$;

$R_1$, which can be the same or different, can be selected from $R_2$, an amine containing group of the formula $—(CH_2)_n—F_{n1}—B_{n2}—F—NH_2$ and a pyrrolidone containing carboxyl functional group of the formula:

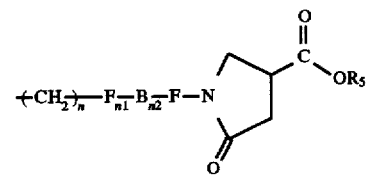

wherein at least one of $R_1$ is a pyrrolidone containing carboxyl or ester functional group or salt derivative thereof as shown; F, which can be the same or different is linear or branched alkylene of 1–12 carbon atoms, preferably ethylene, propylene and isobutylene; $R_2$ is as defined below; $R_5$ can be hydrogen, lower alkyl $(C_{1-6})$ or alkali metal; B is $—NR_9$, oxygen or sulfur, wherein $R_9$ is hydrogen or lower alkyl $(C_{1-6})$; n is zero or 2; $n^1$ is zero or 1; and $n^2$ is zero or 1 with the proviso that when n is zero and $n^2$ is 1, $n^1$ is 1, when n is 2 and $n^2$ is 1, $n^1$ is zero or 1 and when n is 2 and $n^2$ is zero, $n^1$ is zero.

$R_2$ can be the same or different and can be selected from alkyl, aryl, alkenyl, or alkynyl;

$R_3$ and $R_4$, which may be the same or different, are selected from alkyl, aryl, capped or uncapped polyoxyalkylene, alkaryl, aralkylene, alkenyl or alkynyl;

a can be an integer from 0 to 50,000; and b can be an integer from 0 to 100; with the proviso that if a is zero, all $R_1$ groups can be the same and $R_3$ can be the same or different than the $R_2$ group.

In another aspect of the present invention there is provided a method for preparing uncapped silicone fluids containing one or more pyrrolidone-containing functional carboxylic acid groups and/or the ester derivatives thereof, including an amphoteric class of uncapped polysiloxane compositions, which comprises reacting an uncapped organosilicone fluid or composition containing at least one carbofunctional primary amine group with itaconic acid or an ester derivative thereof at an elevated temperature (preferably from about 90° C. to about 130° C.) for a time sufficient to react, preferably substantially completely react (generally ranging from about 1–5 hours), the itaconic acid or ester thereof with the functional primary amine group(s) on the silicone fluid or composition to form an uncapped organosilicone composition having at least one pyrrolidone-containing carboxyl functional group.

In a further aspect of the present invention there is provided a novel silicone-modified amidoamine composition having the formula:

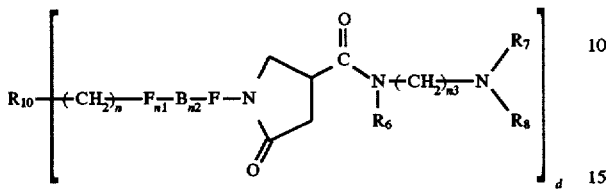

wherein:

$R_{10}$ is the silicone backbone chain as herein described to which at least one pyrrolidone containing amidoamine derivative of a pyrrolidone-containing carboxyl functional group can be attached as shown;

$R_6$ is hydrogen or alkyl, hydroxyalkyl or alkenyl of up to 6 carbon atoms each, cycloalkyl of up to 6 carbon atoms, or polyoxyalkylene of up to 10 carbon atoms within the oxyalkylene unit;

$R_7$ and $R_8$, which may be the same or different, are selected from alkyl, hydroxyalkyl, carboxyalkyl of up to 6 carbon atoms in each alkyl; and polyoxyalkylene of up to 10 carbon atoms; in addition $R_7$ and $R_8$ taken together with the nitrogen to which they are attached may represent an N-heterocycle;

$n^3$ is an integer from 2 to 12;

n is zero or 2;

$n^1$ is zero or 1;

$n^2$ is zero or 1.

B is —$NR_9$, oxygen or sulfur, wherein $R_9$ is hydrogen or lower alkyl ($C_{1-6}$); with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0;

F which can be the same or different is branched or linear alkylene of 1-12 carbon atoms; and d is at least one.

DESCRIPTION OF THE PREFERRED EMBODIMENTS

In accordance with the present invention there are provided novel uncapped polysiloxanes comprising a class of carboxyl-containing uncapped polysiloxanes including an amphoteric class of such polysiloxanes which may be represented by the general formula:

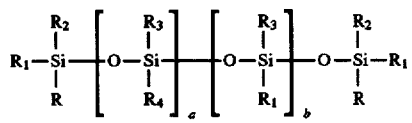

wherein:

R is selected from $R_2$ or $OR_9$ wherein $R_9$ is hydrogen or alkyl, preferably lower alkyl ($c_{1-6}$), with the proviso that at least one of the R groups must be —$OR_9$;

$R_1$, which can be the same or different, can be selected from $R_2$, an amine containing group of the formula —$(CH_2)_n$—$F_n^1$—$B_n^2$—F—$NH_2$ and a pyrrolidone containing carboxyl functional group of the general formula:

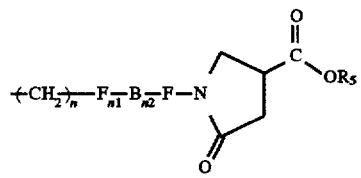

wherein at least one $R_1$ group is a pyrrolidone-containing carboxyl or ester functional group or salt derivative thereof as shown; F, which can be the same or different is linear or branched alkylene of 1-12 carbon atoms, preferably ethylene, propylene and isobutylene; $R_2$ is as defined below; $R_5$ is hydrogen, alkyl, preferably lower alkyl ($C_{1-6}$), or an alkali metal; and B is —$NR_9$, oxygen or sulfur, wherein $R_9$ is hydrogen or alkyl, preferably lower alkyl ($C_{1-6}$); n is zero or 2; $n^1$ is zero or 1; $n^2$ is zero or 1, with the proviso that when n is zero and $n^2$ is 1, $n^1$ is 1, when n is 2 and $n^2$ is 1, $n^1$ is zero or 1 and when n is 2 and $n^2$ is zero, $n^1$ is zero;

$R_2$ can be the same or different and can be selected from alkyl, aryl, alkenyl and alkynyl;

$R_3$ and $R_4$, which may be the same or different are selected from alkyl, aryl, capped or uncapped polyoxyalkylene, alkaryl, aralkylene, alkenyl, or alkynyl;

a can be an integer from 0 to 50,000; and b can be an integer from 0 to 100; with the proviso that if a is zero, all $R_1$ groups can be the same and $R_3$ can be the same or different than the $R_2$ groups.

It is evident from the general formula above that the uncapped polysiloxane compositions of the present invention have one or more carbofunctional pyrrolidone-containing carboxyl or ester group(s) or salt derivative thereof linked terminally, laterally or both terminally and laterally to the silicone (polysiloxane) chain through a hydrocarbon linkage which may contain a hetero nitrogen, oxygen or sulfur atom.

The uncapped polysiloxane compositions including the amphoteric class of such polysiloxanes according to the present invention are useful, for example, for reducing the friction of petroleum flow through pipelines and as additives for personal care products as well as being precursors for a wide range of personal care products, fiber treating agents and the like which impart such advantages as improved feel, substantivity, reduced surface tension, and anti-stick characteristics.

The novel uncapped polysiloxanes including the amphoteric class of polysiloxanes of the present invention surprisingly and unexpectedly can be readily prepared by the reaction of corresponding uncapped silicone compositions or fluids having one or more carbofunctional amine groups including diamine groups, each of which amine group(s) must contain a primary amine group, with up to about one equivalent, preferably about stoichiometric quantities, of itaconic acid or its ester per primary amine group at an elevated temperature for the time sufficient for substantially all of the itaconic acid or its ester to react with the functional primary amine group(s). In general from about 0.5, preferably, from about 0.9 to about 1.1 equivalents of itaconic acid or its ester per functional primary amine group is reacted with the uncapped silicone fluid wherein substantially all the itaconic acid and preferably all the functional primary amine group(s) is reacted and an uncapped polysiloxane composition with at least one carbofunctional pyrrolidone-containing functional carboxyl group(s) and/or its ester or salt is formed.

The reaction can be carried out neat or in an inert solvent such as alcohol, hydrocarbon solvent, chlorinated hydrocarbon and the like, as desired, in general, at elevated temperature up to 175° C., preferably from about 90° C. to about 130° C. The reaction readily proceeds and generally complete reaction of the itaconic acid or its ester with the available functional primary amine group(s) occurs in the Michael Addition Reaction manner, with the double bond of the itaconic acid followed by immediate cyclization to form a pyrrolidone group which will occur in from about 1 to 5 hours. Routine analytical techniques for amine and acid values as well as monitoring viscosity, color and water and/or alcohol evolution can be used to determine completion of the reaction.

Uncapped silicone fluids suitable for use in accordance with the practice of the invention, having one or more carbofunctional primary amine group(s) or diamine group(s) that contain a primary amine group, which may be linked terminally, laterally or both terminally and laterally, as desired, via an alkylene linkage to silicon are well known and are available commercially, for example from Dow Corning, General Electric and Shin-Etsu. Suitable uncapped silicone fluids include alkoxy or hydroxy terminated silicone fluids having one or more primary aminoalkyl functional groups or diamine aminoalkylaminoalkylene functional groups such as methoxy terminated aminoethylaminopropyl functional silicone fluids. While the equivalent weight of the uncapped silicone fluids or compositions which may be employed in the preparation of the pyrrolidone-containing carboxyl functional uncapped polysiloxanes of the present invention is not critical, and suitable compositions may have equivalent weights of 12,000 or even higher, although functional silicone fluids having equivalent weights from about 500 to about 12,000 are in general preferred.

As indicated, the pyrrolidone-containing carboxyl functional uncapped polysiloxane compositions including the amphoteric class of such polysiloxanes of the present invention are readily prepared by reaction of uncapped silicone fluids containing amine or diamine groups wherein each of the diamine groups must contain a primary amine group(s) with itaconic acid or its ester. Itaconic acid (methylene succinic acid) is a compound of the formula:

$$CH_2=C(COOR_9)CH_2COOR_9$$

wherein $R_9$, which can be the same or different, is hydrogen or lower alkyl (1–6 carbon atoms).

The compound itaconic acid is available commercially from Rhone Poulenc and Pfizer Chemicals Division whereas ester derivatives thereof are available from Morflex Inc., Greensboro, N.C. The compounds are produced by known fermentation techniques although chemical synthesis methods are also known.

In another aspect of the present invention, there are provided novel uncapped silicone-containing amidoamine compositions that are suitable for use as surfactants and a variety of other applications as well as intermediate reactants preferably for use in the preparation of derivatives of the novel uncapped polysiloxane compositions of the invention as hereinabove described. The novel amidoamine compositions of the invention may be represented by the general formula:

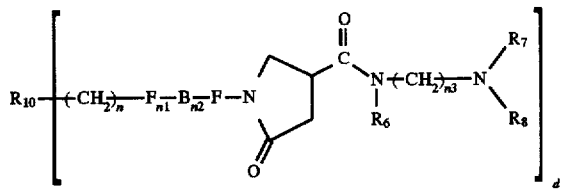

wherein:

$R_{10}$ is an uncapped silicone backbone chain as herein described to which at least one pyrrolidone-containing carboxyl functional group or amidoamine derivative thereof is attached as hereinabove shown;

$R_6$ is hydrogen or alkyl, hydroxyalkyl or alkenyl up to 6 carbon atoms each, cycloalkyl of up to 6 carbon atoms or polyoxyalkylene of up to 10 carbon atoms, preferably from 2 to 5 carbon atoms, within the oxyalkylene unit and at least one $R_6$ is hydrogen;

$R_7$ and $R_8$, which may be the same or different, are selected from alkyl, hydroxyalkyl, carboxyalkyl of up to 6 carbon atoms in each alkyl, and polyoxyalkylene of up to 10 carbon atoms; in addition $R_7$ and $R_8$ taken together with the nitrogen to which they are attached may represent N-heterocycle;

F which can be the same or different is linear or branched alkylene of 1–12 carbon atoms, preferably ethylene, propylene and isobutylene;

B is $-NR_9$, oxygen or sulfur, wherein $R_9$ is hydrogen or lower alkyl ($C_{1-6}$); with the proviso that when n is zero and $n^2$ is 1, $n^1$ is 1, when n is 2 and $n^2$ is 1, $n^1$ is zero or 1 and when n is 2 and $n^2$ is zero, $n^1$ is zero;

n is zero or 2;

$n^1$ is zero or 1;

$n^2$ is zero or 1;

$n^3$ is an integer from 2 to 12; and d is an integer from 1 or greater, generally from 1–50 and preferably 2–10.

The novel silicone-containing amidoamine compositions of the invention can be prepared as follows:

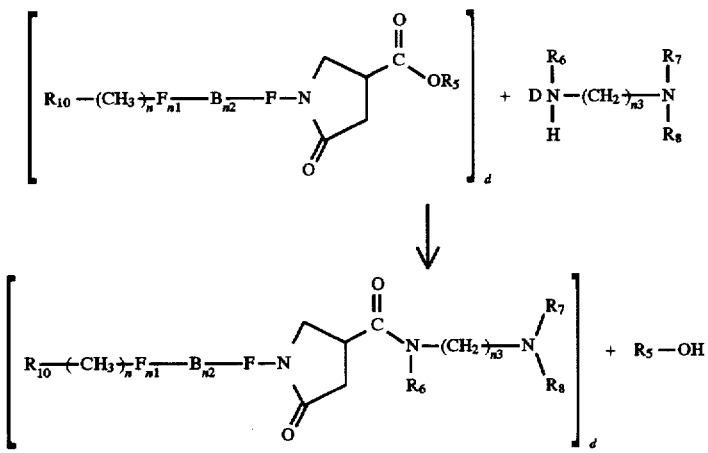

wherein:

- $R_{10}$ is an uncapped silicone backbone chain as herein described to which at least one pyrrolidone-containing carboxyl functional group or amidoamine derivative thereof is attached as hereinabove shown;
- $R_5$ is hydrogen, lower alkyl ($C_{1-6}$) or alkali metal;
- $R_6$ is hydrogen or alkyl, hydroxyalkyl or alkenyl up to 6 carbon atoms each, cycloalkyl of up to 6 carbon atoms or polyoxyalkylene of up to 10 carbon atoms, preferably from 2 to 5 carbon atoms, within the oxyalkylene unit and at least one $R_6$ is hydrogen;
- $R_7$ and $R_8$, which may be the same or different, are selected from alkyl, hydroxyalkyl, carboxyalkyl of up to 6 carbon atoms in each alkyl, and polyoxyalkylene of up to 10 carbon atoms; in addition $R_7$ and $R_8$ taken together with the nitrogen to which they are attached may represent an N-heterocycle;
- F which can be the same or different is linear or branched alkylene of 1–12 carbon atoms;
- B, n, $n^1$, $n^2$ and $n^3$ are as hereinabove defined.
- d and D is an integer from 1 or greater, generally from 1–50 and preferably 2–10. The reactant ratio of the amine reactant to the carboxyl reactant on the silicon is preferably 1:1 but can be varied in ratio from 1:0.8 to 1:1.2.

Uncapped silicone-containing amidoamines of the invention are readily prepared by the above coupling reaction from the novel uncapped polysiloxane compositions of the present invention having one or more pyrrolidone-containing functional carboxyl group(s) as hereinabove described.

The above coupling reaction for preparing the silicone-containing amidoamine compositions can be carried out neat or can be carried out in an inert solvent such as xylene, toluene, chlorobenzene or the like. While the equivalent weight of the silicone-containing amidoamine compositions is not critical, preferably the equivalent weight of such compositions will range from about 500 to 15000.

The novel uncapped polysiloxane compositions having at least one carbofunctional pyrrolidone-containing carboxyl group(s) including the amphoteric class of such polysiloxanes, and the amidoamine derivatives thereof as herein described display many of the well known properties of silicone compositions such as emolliency, detackification, smoothing, lubrication and sufactancy properties while, in addition, making them suitable as precursor reactors for the preparation of a variety of silicone-containing derivatives. In this connection, the novel compositions of the invention are suitable for the preparation of silicone-containing derivative compositions which exhibit the unique property of water-dispersibility or solubility and substantivity.

The preparation of specific compositions of the invention is illustrated by the following specific examples which are provided herein for purposes of illustration only and are not intended to limit the scope thereof.

EXAMPLE 1

This example illustrates the preparation of an uncapped siloxane composition with a lateral or pendant linked carbofunctional pyrrolidone-containing carboxyl group.

One hundred grams of an alpha-omega silanol fluid obtained under the tradename Masil 750 fluid from Mazer Division of P.P.G. are charged to a reaction vessel and admixed with 5 grams of an aminopropropylmethyl diethoxysilane (0.026 moles) obtained from Huls as 1505 Fluid, 1.4 grams of water (0.078 moles) and ½ gram of potassium hydroxide under a nitrogen atmosphere. The reaction mixture is heated to reflux while slowly removing a mixture of ethanol and excess water until the reaction reaches a temperature of 165° C. The reaction is held at 165° C. for 8 hours and then cooled, neutralized with ½ cc of acetic acid and filtered. The reaction mixture forms a clear liquid having an alkali number of 18 which corresponds to an equivalent weight of 3116.6.

A mixture of 50 grams of the amine functional uncapped siloxane fluid prepared above (0.016 moles) and 2.06 grams of itaconic acid are charged to a reaction vessel and slowly heated to 135° C. with agitation. The reaction mixture initially consists of a solid dispersed in the liquid silanol fluid and the reaction proceeds slowly. After about 1 and ½ hours, the reaction mixture becomes homogeneous and is then filtered while still hot.

The reaction product is determined to have an acid number of 22.9 which corresponds to an equivalent weight of 2450. The alkali number of the reaction product is less than one. Both IR and NMR evaluations confirms the presence of a pyrrolidone ring in the reaction product.

EXAMPLE 2

A reaction mixture of 24.5 grams of the uncapped siloxane carboxyl-containing reaction product prepared in Example 1 (0.01 equivalents) and 1.5 grams of Dimethylaminopropylamine (DMAPA) are charged to a reaction vessel under a nitrogen purge and heated slowly to 165° with agitation whereupon a combination of water, excess DMAPA and some cyclics are codistilled. After a period of 4 hours at 165° the acid number of the reaction product is determined to be zero. The reaction mixture is then heated at 100° C. under a vacuum of 30 mm to remove volatiles.

The alkali number of the reaction product is 26.7 which corresponds to an equivalent weight of 2101. IR evaluation shows the reaction product to have silanol end groups and amide absorption.

EXAMPLE 3

This example illustrates the preparation of an alpha, omega functional siloxane homopolymer fluid containing N-(methyloxysilylpropylene)-4-carbomethoxy pyrrolidone repeating units and terminating in a mixture of hydroxyl and/or ethoxy groups.

19.1 grams of gamma aminopropyl-methyl diethoxysilane and 5.4 grams of $H_2O$ are charged to a reaction vessel and stirred at ambient temperature for ½ hour. A mild exotherm occurs which raises the reaction mixture to a temperature of about 42° C. The reaction mixture is then brought to a temperature of 125° C. under atmospheric pressure while removing both water and ethanol. The reaction mixture in the raction vessel is a viscous liquid to which is added 13 grams of itaconic acid while raising the reaction mixture to a temperature of 135° C. The reaction mixture is maintained at 135° C. with agitation for 6 hours with water being continuously removed.

A clear melt reaction product results which does not flow at room temperature. The alkali number of the reaction product is zero and the acid number 224 which corresponds to an equivalent weight of 250.

EXAMPLE 4

242.8 grams of a Dimethyl silanol capped Dimethyl fluid (0.1 molar equivalent) and 38.2 grams (10.3 mols) of aminopropyl methyldiethoxy silane are charged with 0.2 grams potassuim hydroxide to a reaction vessel and heated under a nitrogen purge, with agitation, to reflux temperature. Ethanol formed by the condensation reaction is removed and collected. After a period of 5 hours a total of 8.9 grams are collected. A uniform, colorless liquid is formed having an amine content of 1.3 percent which corresponds to a molecular weight of 2832. IR confirms that the silicone fluid is capped with an ethoxy group, NMR confirms that the silicone fluid is primarily an alpha, omega bis aminopropyl ethoxy methyl capped Dimethyl siloxy fluid.

To 28.32 grams of the silicone fluid prepared above (0.01 mole) is added 3.16 grams of Dimethyl itaconate (0.02 moles) in a reaction vessel, with agitation. The reaction mixture is heated to 135°–140° C. whereupon the reaction mixture has a single phase and alcohol is evolved. The reaction mixture is heated for a period of 2–3 hours during which alcohol evolves. The alkali number of the reaction product is zero indicating complete reaction of the amino groups. IR of the reaction products shows ester groups are present and the silicone fluid is alkoxy capped.

EXAMPLE 5

A mixture of 166 grams of a methoxy terminated functional diamine silicone fluid obtained under the tradename KF857 from Shin-Etsu and 15.8 grams of Dimethyl Itaconate are charged to a reaction vessel and heated to 135°–140° C., with agitation, under a nitrogen sparge for 3–4 hours. Methanol is continuously removed from the reaction vessel. A clear amber fluid results having an alkali number of 34 as compared to an alkali number of 626 in the original fluid. IR showed ester absorption in the reaction product.

Two grams of Dimethylaminopropylamine (DMAPA) are added to the reaction mixture above and the reaction mixture is heated to 170°–175° C. Methonal evolves from the reaction mixture and a less viscous fluid forms after 4 hours of reaction. The reaction product is vacuum stripped at 30 mm pressure at a termperature of 100° C. to remove excess DMAPA.

The alkali number of the reaction product is 58.

What is claimed is:

1. A polysiloxane composition having the formula

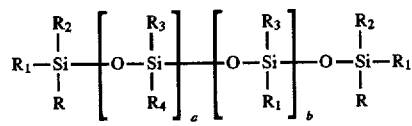

wherein:

R is selected from $R_2$ or $-OR_9$, wherein $R_9$ is hydrogen or alkyl, with the proviso that at least one of the R groups is $-OR_9$.

$R_1$, which can be the same or different, is selected from $R_2$, an amine containing group of the formula $-(CH_2)-F_{n1}-B_{n2}-F-NH_2$ or a pyrrolidone-containing functional carboxyl group of the general formula:

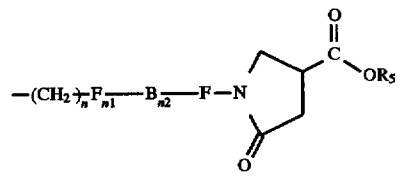

wherein at least one $R_1$ is the pyrrolidone containing functional carboxyl group or derivative thereof as shown; $R_2$ is as defined below; $R_5$ is hydrogen, lower alkyl ($C_{1-6}$) or alkali metal; F which can be the same or different, is linear or branched alkylene of 1–12 carbon atoms; B is $-NR_9$, oxygen or sulfur wherein $R_9$ is hydrogen or lower alkyl ($C_{1-6}$); n is zero or 2; $n^1$ is zero or 1, an $n^2$ is zero or 1 with the proviso that when n is zero and $n^2$ is 1, $n^1$ is 1, when n is 2 and $n^2$ is 1, $n^1$ is zero or 1 and when n is 2 and $n^2$ is zero, $n^1$ is zero.

$R_2$ can be the same or different and is selected from alkyl, aryl, alkenyl or alkynyl.

$R_3$ and $R_4$, which may be the same or different are selected from alkyl, aryl, capped or uncapped polyoxyalkylene, alkaryl, aralkylene, alkenyl or alkynyl;

a is an integer from 0 to 50,000; and b is an integer from 0 to 100.

2. The polysiloxane composition as claimed in claim 1, wherein $R_5$ is hydrogen or lower alkyl.

3. The polysiloxane composition as claimed in claim 1, wherein $R_1$ is $R_2$ or the pyrrolidone-containing carboxyl functional group or derivative thereof and at least one of $R_1$ is the pyrrolidone-containing carboxyl functional group or derivative thereof.

4. The polysiloxane composition as claimed in claim 1, wherein at least one terminally linked $R_1$ group is the pyrrolidone containing carboxyl functional group or derivative thereof.

5. The polysiloxane composition as claimed in claim 1, wherein $R_3$ and $R_4$ are methyl and a is at least 1.

6. The polysiloxane composition as claimed in claim 1, wherein both terminal $R_1$ groups are $R_2$ and a and b are each at least 1.

7. The polysiloxane composition as claimed in claim 1, wherein $R_2$, $R_3$ and $R_4$ are methyl.

8. The polysiloxane composition as claimed in claim 1, wherein $R_9$ in the $R_1$ group is hydrogen.

9. The polysiloxane composition is claimed in claim 1, wherein when a is zero, all the $R_1$ groups are the same.

10. The polysiloxane composition as claimed in claim 1, wherein when a is zero, the $R_3$ groups can be the same or different than the $R_2$ groups.

11. The polysiloxane composition as claimed in claim 1, wherein when a is zero, the $R_3$ groups are the same as the $R_2$ groups.

12. The polysiloxane composition as claimed in claim 1, wherein B is $-NR_9$.

13. A method for preparing uncapped polysiloxane compositions containing at least one pyrrolidone-containing carboxyl functional group or the ester derivatives thereof, which comprises reacting an uncapped organosilicone composition having at least one terminal hydroxy or alkoxy group and at least one amine functional group containing a primary amine group with at least about 0.5 equivalents of itaconic acid or an ester derivative thereof at an elevated temperature for a time sufficient to react substantially all the itaconic acid or ester derivative thereof with the primary amine group(s) on the silicone composition and to form an organosilicone composition having at least one terminal hydroxy or alkoxy group and at least one pyrrolidone containing carboxyl functional group.

14. The method for preparing polysiloxane compositions as claimed in claim 13, wherein said organosilicone composition having at least one amine functional group containing a primary amine group is substantially compatible with said itaconic acid or ester derivative thereof at the reaction temperature and forms a homogeneous reaction mixture therewith.

15. The method for preparing polysiloxane compositions as claimed in claim 13, wherein reaction of said organosilicone composition having at least one amine functional group and itaconic acid or ester is carried out at a temperature from about 90° C. to about 130° C.

16. The method for preparing polysiloxane compositions as claimed in claim 13, wherein about a stoichiometric amount of itaconic acid or its ester derivative per primary amine group on the functional amine group(s) is employed in said reaction.

17. The method for preparing polysiloxane compositions as claimed in claim 13, wherein said organosilicone composition has one or more terminal or lateral amine functional groups.

18. A silicone-containing amidoamine composition having the formula:

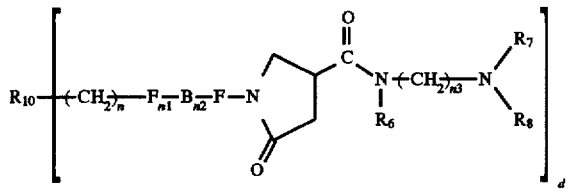

wherein:

$R_{10}$ is a silicone backbone chain to which at least one pyrrolidone-containing amidoamine derivative of a pyrrolidone-containing carboxyl functional group as shown can be attached;

$R_6$ is hydrogen or alkyl, hydroxyalkyl or alkenyl of up to 6 carbon atoms each, cycloalkyl of up to 6 carbon atoms, or polyoxyalkylene of up to 10 carbon atoms within the oxyalkylene unit;

$R_7$ and $R_8$, which may be the same or different, are selected from alkyl, hydroxyalkyl, cycloalkyl or carboxyalkyl of up to 6 carbon atoms in each alkyl or polyoxalkylene of up to 10 carbon atoms; or in addition $R_7$ and $R_8$ taken together with the nitrogen to which they are attached represents an N-heterocycle.

F which can be the same or different is linear or branched alkylene of 1–12 carbon atoms;

n is zero or 2.

$n^1$ is zero or 1.

$n^2$ is zero or 1.

$n^3$ is at least 1;

B is $-NR_9$, oxygen or sulfur, wherein $R_9$ is hydrogen or lower alkyl; with the proviso that when n is zero and $n^2$ is 1, $n^1$ is 1, when n is 2 and $n^2$ is 1, $n^1$ is zero or 1 and when n is 2 and $n^2$ is zero, $n^1$ is zero; and d is at least one.

19. A personal care and cosmetic composition comprising at least 0.1% of an uncapped polysiloxane composition having at least one terminal hydroxy or alkoxy group and at least one pyrrolidone-containing functional carboxyl group or derivative thereof as claimed in claim 1.

* * * * *

UNITED STATES PATENT AND TRADEMARK OFFICE
CERTIFICATE OF CORRECTION

PATENT NO.   : 5,736,583
DATED        : April 7, 1998
INVENTOR(S)  : Fost and Berger It is certified that error appears in the above-identified patent and that said Letters Patent is hereby corrected as shown below:

Column 12,
Lines 5-43, delete Claim 18

Signed and Sealed this

Twenty-eighth Day of October, 2003

JAMES E. ROGAN
*Director of the United States Patent and Trademark Office*